United States Patent [19]

Clayton

[11] Patent Number: 4,775,532

[45] Date of Patent: Oct. 4, 1988

[54] ANIMAL REPELLANT COMPOSITION

[75] Inventor: William J. Clayton, Fairport, N.Y.

[73] Assignee: Mobil Oil Corporation, New York, N.Y.

[21] Appl. No.: 664,095

[22] Filed: Oct. 24, 1984

Related U.S. Application Data

[63] Continuation of Ser. No. 484,798, Apr. 14, 1919, abandoned.

[51] Int. Cl.$^4$ ............................................. A61K 35/78
[52] U.S. Cl. .................................................. 424/195.1
[58] Field of Search ............................. 424/195, 195.1

[56] References Cited

U.S. PATENT DOCUMENTS 3,474,176 10/1969 Freeman .............................. 424/331
4,169,898 10/1979 Hasse et al. ......................... 424/331

OTHER PUBLICATIONS

*Chem. Absts.* 95: 182280h, 1981.

*Primary Examiner*—John Rollins
*Attorney, Agent, or Firm*—Alexander J McKillop; Michael G. Gilman; James P. O'Sullivan, Sr.

[57] ABSTRACT

An animal repellent composition comprising an animal repellent proportion of an olfactory animal repellent carried by a vehicle comprising a di(alkhyl) adipate and a method of repelling animals.

12 Claims, No Drawings ns
ANIMAL REPELLANT COMPOSITION

This is a continuation of copending application Ser. No. 484,798, filed on Apr. 14, 1983 now abandoned.

BACKGROUND OF THE INVENTION

This invention is generally concerned with compositions and methods of controlling animals and, more particularly, is directed to a novel composition for repelling animals and, in particular, dogs and cats.

For reasons of health and convenience, it has frequently been found to be desirable to discourage animals from frequenting certain areas. For example, garbage receptacles become both an unpleasant chore to handle and a serious potential health hazard after being ravaged by domestic animals, such as dogs and cats or by non-domestic animals, such as mice, rats, coyotes, wolves, or the like.

Chemical agents are commonly employed to discourage such animals from approaching those areas from which mankind finds it desirable to exclude them, but, while there are many chemical compounds which would effectively repel ravaging animals, there are two restrictions which severely limit the number of chemicals actually available for use. The first restriction is toxicity: the compound used must be substantially, and preferably completely, non-toxic to mammals since they will frequently be used in proximity to small children and household pets, and the probability of contact and ingestion is high. The second restriction lies with the odor of the compound: if the agent is such that it is repulsive or even unpleasant to humans, then it will not be suitable for use in populated areas. Among the relatively few compounds which meet these strictures and are known to have at least some ability to repulse animals are methyl nonyl ketone, see U.S. Pat. No. 3,474,176 and Canadian Pat. No. 978,475; and cinnamaldehyde, see Journal of Wildlife Management, 40 (1): 1976 pp 145–150 and for combinations of the two compounds as an animal repellent see U.S. Pat. No. 4,169,898.

It has been discovered that certain common materials, e.g. mineral oil, employed as a vehicle for olfactory animal repellents, such as cinnamic aldehyde and methyl nonyl ketone, do not dissolve the repellent. Thus, as soon as such a mixture is sprayed onto, for example, a bag, separation occurs. In addition, mineral oil is quite soluble to polyethylene, a common bag material, and hence, it is absorbed readily by the bag. As a result of this effect, there is no vehicle to hold the active ingredients after a few hours of elapsed time. Consequently, the active ingredients evaporate in a short period and are not available to repel animals.

SUMMARY OF THE INVENTION

It has now been discovered that olfactory animal repellents can be effectively transported over surfaces by means of a vehicle comprising a liquid di(alkyl)adipate i.e. esters of adipic acid. It has also been discovered that olfactory animal repellents can be effectively transported over surfaces by means of a combination of a liquid di(alkyl)adipate and a sodium di-$C_4$–$C_{13}$ alkylsulfosuccinate.

The present invention is also directed to a method for repelling animals which comprises exposing an animal to the above-identified repellent compositions.

DESCRIPTION OF THE PREFERRED EMBODIMENTS

The liquid di(alkyl)adipates contemplated by the present invention include those having alkyl groups having from 1–10 carbon atoms. These compounds are the diesters of adipic acid. The alkyl group of the ester can be the same or two different alkyl groups may be present in the same ester. Furthermore, mixtures of di(alkyl)adipates are also contemplated. The following esters of adipic acid exemplify this class of vehicles: di(isobutyl)adipate, di(butyl)adipate, di(ethyl)adipate, di(2-ethylbutyl)adipate, di(2-ethylhexyl)adipate, di(methyl)adipate, di(propyl)adipate, di(isopropyl)adipate, particularly preferred is di(n-heptyl,n-nonyl)adipate.

Contemplated olfactory animal repellents include cinnamic aldehyde, methyl nonyl ketone, essence of red pepper, otherwise known as capsicum (capsaicin is the pungent principle of Tobasco, cayenne or red pepper) and quinine. Cinnamic aldehyde and methyl nonyl ketone individually or in combination are effectively transported over surfaces in combination with the above-identified adipates. When essence of red pepper or quinine is employed the effectiveness of the combination is significantly enhanced by the inclusion therein of a sodium di-$C_4$-$C_{13}$ alkylsulfosuccinate. Contemplated di alkyl groups include the same or different $C_4$ to $C_{13}$ alkyl groups, for example, isobutyl, hexyl, octyl, and tri-decyl. Particularly preferred is sodium di tri-decyl-sulfosuccinate.

The contemplated compositions are broadly directed to an animal repellent composition comprising an animal repellent proportion of the olfactory animal repellent carried by a vehicle comprising the above-identified adipate. The proportions of the vehicle and repellent are effective over a broad range, however, a particularly preferred proportion of the vehicle is from about 70 to 95% by weight and a preferred percentage of said repellent is from about 5 to about 30% by weight of said composition. The olfactory repellent can be employed alone or in combination with one or more other repellents in the composition. A preferred ratio when a combined olfactory repellent is employed is from 1 to 4 parts of one of the repellents to from 1 to 4 parts of the other repellent. A particularly preferred composition is from about 1 to 4 parts methyl nonyl-ketone to about 1 to 4 parts of cinnamic aldehyde. When essence of red pepper or quinine is employed as the olfactory repellent it is preferred to also employ the above-identified sulfosuccinate. The sulfosuccinate can be present in the vehicle in from about 5 to 30% by weight of the vehicle.

It is contemplated that the compositions of the present invention will be especially useful when applied to containers for discarded edible refuse, as would commonly be present in homes and restaurants. Such containers may be metal or plastic garbage cans, plastic bags, paper and cardboard boxes and the like. For the purposes of this disclosure, any conventional container which might be used to hold edible refuse, and thereby be subject to be ravaged by a hungry animal in search of food, is considered suitable for application of the repellent compositions herein disclosed. Such application may be by liquid application, by means of a spray applicator of the pump type, or an aerosol-type spray can containing, in addition to the repellent agents and the subject carrier, a conventional self-propellant composition e.g. a low boiling hydrocarbon or its equivalent. It is expected that the application would be directed to the outside of the container itself, but it is foreseeable that such repellent may be beneficially applied to the area immediately surrounding such containers, or mixed with the contents of the container.

The experimental data set forth hereinbelow shows the results of applying the subject repellent to plastic bags containing an odoriferous food and old newspapers versus old newspapers alone. In some cases the repellent was applied only outside the bag, in some cases only inside the bag, in some cases inside and outside and in some cases no repellent was employed.

The bags employed were commercially available polyethylene garbage bags. Seven series of bags were employed. Test bags L-O were filed with crushed newspapers and no repellent was applied to or used in these bags. Test bags L-5A consisted of bags which contained half a bag load of newspapers, half of a 15 oz. can of mackeral and another half a bag load of newspapers. The L-5A bags were not treated with repellent. An identical series of bags, L-5B bags, contained the same arrangement of newspapers and fish but were treated inside and out with 0.75 grams of a composition having the following ingredients:
di(n-heptyl, n-nonyl)adipate: 67.78 pts
cinnamic aldehyde: 16.48 pts
methyl nonyl ketone: 3.27 pts.

Test bags L-6A and L-6B were prepared with the same arrangement of newspapers and mackeral. The L-6B bags were treated on the outside only with 1.5 grams of the above-identified repellent.

Test bags L-7A and L-7B were also prepared as above except that L-7B was treated on the inside only with 1.5 grams of the above-identified repellent composition.

At the beginning of the test, bags filled with crushed newspaper alone were placed in pens with individual test dogs who had not been fed for 24 hours. The dogs were allowed one hour to attack the bag. All dogs which attacked the test bags severly were used in subsequent tests. Occasionally it was necessary to also use a few dogs which attacked bags only moderately.

The definition of the degree of damage done to the bags by the dogs is as follows:
None—no marks on bags
Slight—small tear but no loss of contents.
Moderate—moderate tear but limited loss of contents.
Severe—destroyed bag scattered contents.

At about 1:00 P.M., the day before the test, both series of bags were prepared. This permitted the odor of the fish to increase and become pervasive. At 7:00 A.M. next day, before the dog was fed, an A and B bag was placed in the pen of a dog which previously attacked a newspaper-containing bag either severely or moderately. After one hour the damage to the bag was classified as follows:

| Bag Series | | | Total Bags | None | Slight | Moderate | Severe |
|---|---|---|---|---|---|---|---|
| L-0 | | - newspaper only | 107 | 62 | 2 | 13 | 28 |
| L-5 | A | - w/o repellent | 27 | 15 | 1 | 5 | 6 |
| | B | - with repellent | 27 | 20 | 4 | 2 | 1 |
| L-6 | A | - w/o repellent | 5 | 1 | — | 2 | 2 |
| | B | - with repellent | 5 | 3 | — | 2 | 0 |
| L-7 | A | - w/o repellent | 29 | 4 | 1 | 7 | 16 |
| | B | - with repellent | 29 | 15 | 7 | 6 | 0 |

The foregoing test data shows that the active components of the repellent compositions were effectively applied to the surfaces of the plastic bags via the ester adipate vehicle.

What is claimed is:

1. An animal repellent composition comprising an animal repellent proportion of an olfactory animal repellent carried by a vehicle comprising a liquid di(alkyl)adipate wherein said alkyl group has from 1–10 carbon atoms.

2. The composition of claim 1 comprising from about 70–95% by weight of said vehicle and from about 5–30% by weight of said olfactory repellent.

3. The repellent composition of claim 2 wherein said adipate is di(n-heptyl,n-noyl)adipate.

4. The repellent composition of claim 3 wherein said repellent is a member selected from the group consisting of cinnamic aldehyde, methyl nonyl ketone, essence of red pepper, quinine and mixtures thereof.

5. The repellent composition of claim 4 wherein said repellent is methyl nonyl ketone.

6. The repellent composition of claim 4 wherein said repellent is cinnamic aldehyde.

7. The repellent composition of claim 4 wherein said repellent is a mixture of cinnamic aldehyde and methyl nonyl ketone.

8. The repellent composition of claim 7 wherein said repellent comprises a mixture of from about 1 to 4 parts methyl nonyl ketone to from about 1 to 4 parts cinnamic aldehyde.

9. The composition of claim 2 wherein said vehicle includes a major amount of said adipate and a minor amount of a sodium di-$C_4$-$C_{13}$ alkylsulfosuccinate.

10. The composition of claim 9 wherein said sulfosuccinate is present in from about 5–30% by weight of said vehicle.

11. The method for repelling animals which comprises exposing an animal to the repellent composition of claim 1.

12. The method for repelling animals which comprises exposing an animal to the repellent composition of claim 9.

* * * * *

UNITED STATES PATENT AND TRADEMARK OFFICE
CERTIFICATE OF CORRECTION

PATENT NO. : 4,775,532
DATED : Oct. 4, 1988
INVENTOR(S) : William J. Clayton

It is certified that error appears in the above—identified patent and that said Letters Patent is hereby corrected as shown below:

Cover Sheet, Title - "Repellant" should be --Repellent--

Abstract - "di(alkhyl)" should be --di(alkyl)--

Column 1, line 1 - "Repellant" should be --Repellent--

Column 4, line 32, Claim 4, "n-noyl" should be --n-nonyl--

Cover Sheet, Related Appln. - "1919" should be --1983--.

Signed and Sealed this

Eleventh Day of April, 1989

Attest:

DONALD J. QUIGG

Attesting Officer

Commissioner of Patents and Trademarks